United States Patent
Kumar et al.

(10) Patent No.: US 9,737,263 B1
(45) Date of Patent: Aug. 22, 2017

(54) FOOTWEAR FOR MONITORING HEALTH CONDITION OF FOOT OF A USER AND A METHOD THEREOF

(71) Applicant: Wipro Limited, Bangalore (IN)

(72) Inventors: Vijay Kumar, Bangalore (IN); Santhosh Kumar Madathil, Bangalore (IN); Thomas Chittakattu Ninan, Kannur District (IN)

(73) Assignee: WIPRO LIMITED, Bangalore (IN)

( * ) Notice: Subject to any disclaimer, the term of this patent is extended or adjusted under 35 U.S.C. 154(b) by 25 days.

(21) Appl. No.: 15/083,865

(22) Filed: Mar. 29, 2016

(30) Foreign Application Priority Data

Feb. 15, 2016 (IN) .............................. 201641005248

(51) Int. Cl.
*A61B 5/00* (2006.01)

(52) U.S. Cl.
CPC .......... *A61B 5/6829* (2013.01); *A61B 5/0077* (2013.01); *A61B 5/0082* (2013.01); *A61B 5/6807* (2013.01); *A61B 5/7275* (2013.01); *A61B 5/004* (2013.01)

(58) Field of Classification Search
None
See application file for complete search history.

(56) References Cited

U.S. PATENT DOCUMENTS

| | | | | |
|---|---|---|---|---|
| 5,678,566 A | * | 10/1997 | Dribbon | A43B 17/00 600/549 |
| 8,603,013 B2 | * | 12/2013 | Randolph | A43B 3/0005 600/587 |
| 8,868,157 B1 | * | 10/2014 | Soliz | A61B 5/0077 600/474 |
| 9,019,359 B2 | * | 4/2015 | Leedy | A43D 1/025 348/77 |
| 9,095,305 B2 | * | 8/2015 | Engler | A61B 5/447 |
| 2005/0097762 A1 | * | 5/2005 | Biesbrouck | A61B 5/1074 33/3 R |
| 2011/0288379 A1 | | 11/2011 | Wu | |
| 2012/0212339 A1 | | 8/2012 | Goldblatt | |

(Continued)

FOREIGN PATENT DOCUMENTS

| WO | WO 2004/002309 A1 | 1/2004 |
|---|---|---|
| WO | WO 2010/128519 A1 | 11/2010 |
| WO | WO 2013/049667 A1 | 4/2013 |

*Primary Examiner* — Kennedy Schaetzle
(74) *Attorney, Agent, or Firm* — Finnegan, Henderson, Farabow, Garrett & Dunner LLP (57) ABSTRACT

The present disclosure relates to footwear for monitoring health condition of foot of a user. The footwear comprises one or more image capturing devices and a control unit. The image capturing devices are placed at predefined locations in the footwear to capture one or more images of the foot, when the user is wearing the footwear. The control unit is configured to receive the captured images from the image capturing devices. The captured images are compared with one or more pre-stored images of a healthy foot to identify differences between the captured images and the pre-stored images. The control unit detects health condition of the foot of the user based on the differences. Further, the control unit provides a notification about the health condition of the foot to a computing device associated with the user or one or more care providers of the user.

22 Claims, 5 Drawing Sheets

(56) References Cited

U.S. PATENT DOCUMENTS

| | | | |
|---|---|---|---|
| 2014/0200486 A1* | 7/2014 | Bechtel | A61B 5/14551 600/592 |
| 2015/0133754 A1* | 5/2015 | Freeman | A61B 5/1036 600/323 |
| 2015/0190085 A1 | 7/2015 | Nathan et al. | |
| 2016/0192862 A1* | 7/2016 | Merrell | A61B 5/1038 600/592 |
| 2016/0206242 A1* | 7/2016 | Esposito | A61B 5/1038 |

\* cited by examiner

FOOTWEAR FOR MONITORING HEALTH CONDITION OF FOOT OF A USER AND A METHOD THEREOF

TECHNICAL FIELD

The present subject matter is related, in general to monitoring foot conditions, and more particularly, but not exclusively to a footwear and a method for monitoring health condition of foot of a user when the user is wearing the footwear.

BACKGROUND

Diseases of the foot are generally not limited to the foot itself, instead they manifest elsewhere in the body of the person. Some of the foot diseases may be present with just a mild ache, but few other foot diseases can be very severe and may even limit the person's ability to walk or bear body weight. In most of the cases, home care treatments are sufficient for minor foot diseases except when a severe pain is present as a disabling condition and usually needs some type of medical attention.

However, there are a numerous foot diseases which are not easily identified and get into a critical condition due to lack of right treatment at the right time. An example of such a foot disease is diabetic foot ulcer. Diabetes patients often suffer from diabetic neuropathy which causes numbness and loss of sensation in the toes, feet, legs and palms of the patients. And, as a result, the injury in the foot goes unnoticed and eventually becomes a portal for entry of bacteria and infection. Identifying such foot ulcers at their initial stage helps to avail the right treatment at the right time.

Another example of such a foot disease is 'Gout', which is a kind of arthritis which can cause an attack of sudden burning pain, stiffness, and swelling in a joint, usually a big toe. The most common sign of gout is a nighttime attack of swelling, tenderness, redness, and sharp pain in the big toe. The monitoring of foot to identify the deformations/inflammations due to gout helps in availing the right treatment at the right time. Similar principles can be applied to Rheumatoid arthritis and other progressive, degenerative foot diseases.

The existing arts disclose one or more special apparatus for capturing the images of the foot of the patient to detect the diseases/disorders in the foot. However, the existing arts do not continuously monitor the foot and the progress of the diseases in the foot. Continuous monitoring of the foot is necessary for an early detection and treatment of the diseases/disorders of the foot. Also, the existing arts demand additional efforts from the patients in monitoring/detecting the diseases in the foot, thereby causing inconvenience to the patients. Hence, there is a need for a means which can continuously monitor the foot of the patients without causing any inconvenience to the patients.

The issues mainly faced in monitoring health condition of the foot of a user are capturing the images of the foot of the user and continuously monitoring the condition of the foot for timely detection of foot diseases and providing a notification about the detection of the foot disease in real time.

SUMMARY

Disclosed herein is footwear for monitoring health condition of foot of a user. The footwear is designed to address the one or more foot diseases and/or problems in the foot of the user at an early stage. The footwear would periodically capture images of the foot and compare the captured images with historic images of the foot to detect one or more diseases in the foot. The footwear would also notify the users and/or care providers of the users whenever it detects a visually identifiable disease in the foot.

Accordingly, the present disclosure relates to footwear for monitoring health condition of foot of a user. The footwear comprises one or more image capturing devices and a control unit. The one or more image capturing devices are placed at predefined locations in the footwear to capture one or more images of the foot of the user, when the user is wearing the footwear. The control unit is configured to receive the one or more images from the one or more image capturing devices. The control unit compares the one or more captured images with one or more pre-stored images to identify one or more differences between the one or more captured images and the one or more pre-stored images, wherein the one or more pre-stored images are the images of healthy foot of the user. Upon comparing the images, the control unit detects health condition of the foot of the user based on the one or more differences in the comparison. Further, the control unit provides a notification about the health condition of the foot to a computing device associated with at least one of the user and one or more care providers of the user.

Further, the present disclosure relates to a method for monitoring health condition of foot of a user. The method comprises capturing one or more images of the foot of the user by one or more image capturing devices placed at predefined locations in the footwear. The one or more images are captured when the user is wearing the footwear. The one or more images are received from the one or more image capturing devices by a control unit configured in the footwear. The one or more captured images are compared, by the control unit, with one or more pre-stored images to identify one or more differences between the one or more captured images and the one or more pre-stored images, wherein the one or more pre-stored images are the images of healthy foot of the user. The health condition of the foot of the user is detected based on the comparison. Further, a notification is provided to a computing device associated with at least one of the user and one or more care providers of the user, wherein the notification is about the health condition of the foot of the user.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE ACCOMPANYING DRAWINGS

The accompanying drawings, which are incorporated in and constitute a part of this disclosure, illustrate exemplary embodiments and, together with the description, serve to explain the disclosed principles. In the figures, the left-most digit(s) of a reference number identifies the figure in which the reference number first appears. The same numbers are used throughout the figures to reference like features and components. Some embodiments of system and/or methods in accordance with embodiments of the present subject matter are now described, by way of example only, and with reference to the accompanying figures, in which.

It should be appreciated by those skilled in the art that any block diagrams herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and executed by a computer or processor, whether or not such computer or processor is explicitly shown.

DETAILED DESCRIPTION

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

While the disclosure is susceptible to various modifications and alternative forms, specific embodiment thereof has been shown by way of example in the drawings and will be described in detail below. It should be understood, however that it is not intended to limit the disclosure to the particular forms disclosed, but on the contrary, the disclosure is to cover all modifications, equivalents, and alternative falling within the spirit and the scope of the disclosure.

The terms "comprises", "comprising", or any other variations thereof, are intended to cover a non-exclusive inclusion, such that a setup, device or method that comprises a list of components or steps does not include only those components or steps but may include other components or steps not expressly listed or inherent to such setup or device or method. In other words, one or more elements in a system or apparatus proceeded by "comprises . . . a" does not, without more constraints, preclude the existence of other elements or additional elements in the system or method.

The present disclosure relates to footwear for monitoring health condition of foot of a user. The footwear comprises one or more image capturing devices and a control unit. The one or more image capturing devices are placed at predefined locations in the footwear to capture one or more images of the foot of the user, when the user is wearing the footwear. The control unit is configured to receive the one or more images from the one or more image capturing devices. The control unit compares the one or more captured images with one or more pre-stored images to identify one or more differences between the one or more captured images and the one or more pre-stored images, wherein the one or more pre-stored images are the images of healthy foot of the user. Upon comparing the images, the control unit detects health condition of the foot of the user based on the one or more differences. Further, the control unit provides a notification about the health condition of the foot of the user to a computing device associated with at least one of the user and one or more care providers of the user.

In the following detailed description of the embodiments of the disclosure, reference is made to the accompanying drawings that form a part hereof, and in which are shown by way of illustration specific embodiments in which the disclosure may be practiced. These embodiments are described in sufficient detail to enable those skilled in the art to practice the disclosure, and it is to be understood that other embodiments may be utilized and that changes may be made without departing from the scope of the present disclosure. The following description is, therefore, not to be taken in a limiting sense.

Figure 1:
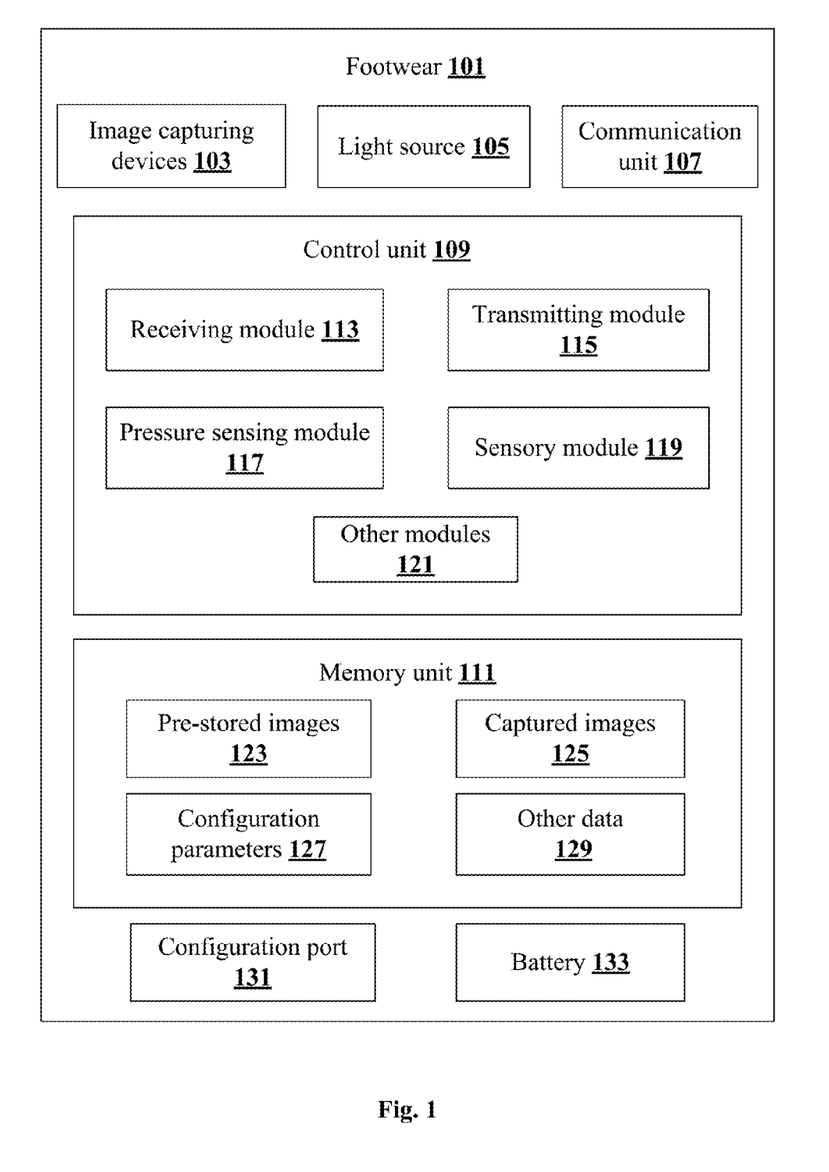
FIG. 1 shows a detailed block diagram illustrating footwear for monitoring health condition of foot of a user in accordance with some embodiments of the present disclosure.

FIG. 1 shows a detailed block diagram illustrating footwear for monitoring health condition of foot of a user in accordance with some embodiments of the present disclosure.

Figure 3A:
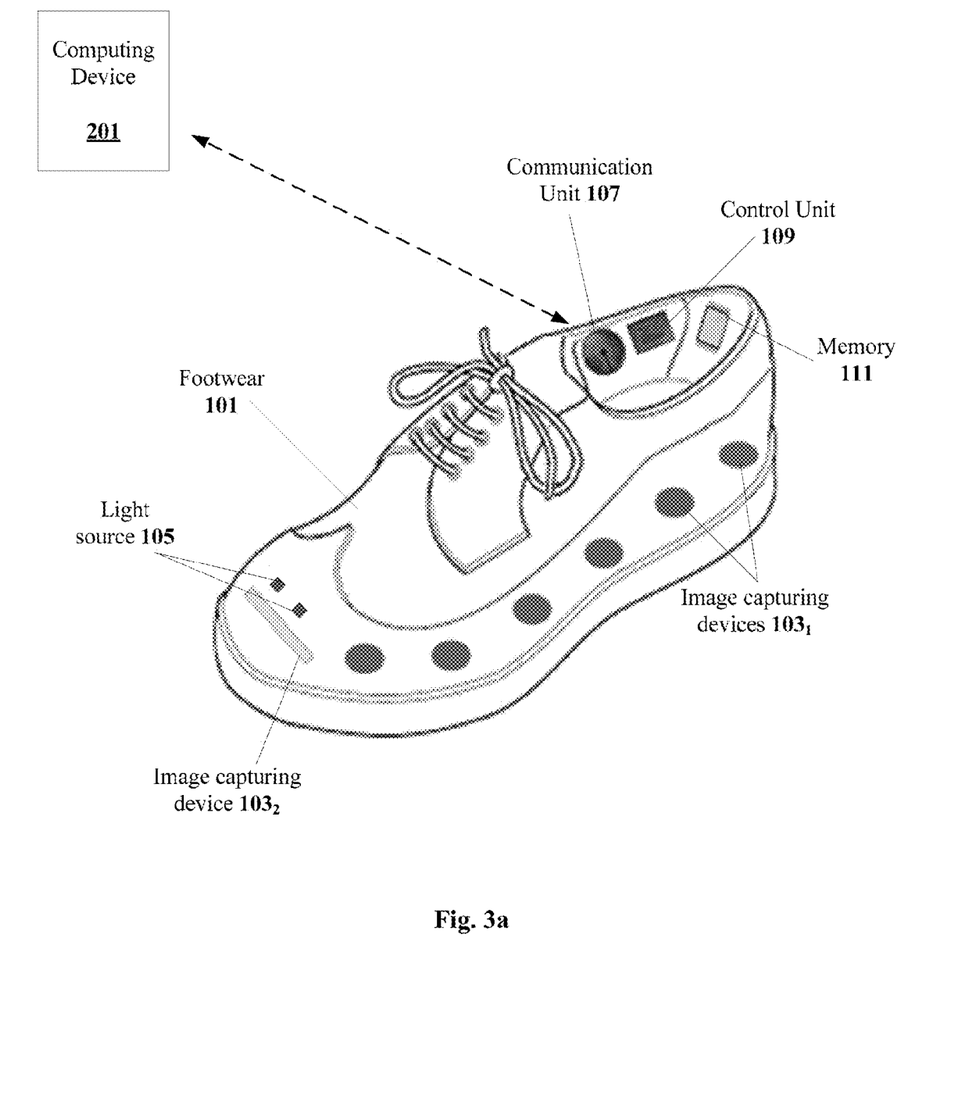
FIGS. 3a and 3b show exemplary representations of the footwear in accordance with some embodiments of the present disclosure.

In an implementation, as shown in FIG. 3a, the footwear 101 comprises one or more image capturing devices 103, a communication unit 107, a control unit 109 and a memory unit 111. In an embodiment, the footwear 101 shall have all the features of any usual footwear 101. Additionally, the footwear 101 shall accommodate all the components described below, for monitoring the health condition of the foot of the user.

In an embodiment, the one or more image capturing devices 103 capture one or more images of the foot of the user when the user is wearing the footwear 101. The one or more image capturing devices 103 may include, but not limiting to, one or more cameras $103_1$ and an image scanner $103_2$. The one or more cameras $103_1$ are placed inside the footwear 101 at one or more predefined location as shown in FIG. 3a to capture one or more images of the foot. Alternatively, the image scanner $103_2$ may be placed and configured in such a way that, the image scanner $103_2$ moves below the foot of the user, thereby capturing one or more images of the foot. In an embodiment, there may be a transparent and/or translucent layer between the one or more image capturing devices 103 and the foot of the user. The transparent and/or translucent layer (not shown in Figs.) placed in the footwear 101 separates the one or more image capturing devices 103 from the foot of the user when the user is wearing the footwear 101, thereby enabling the one or more image capturing devices 103 to capture one or more images of the foot.

The light source 105 (shown in FIGS. 3a and 3b) illuminates the foot of the user for enabling the one or more image capturing devices 103 to capture a clear and bright image of the foot. In an embodiment, the light source 105 may include, without limiting to, a Light Emitting Diode (LED) flash light or a flashcube that may be placed inside the footwear 101. The light source 105 may be synchronized with the one or more image capturing devices 103 for illuminating the footwear 101 only when the one or more image capturing devices 103 are actuated. In an embodiment, the light source 105 may continuously illuminate the inside portion of the footwear 101. Alternatively, the light source 105 may also illuminate the inside portion of the footwear 101 periodically, for a predetermined time interval. As an example, the predetermined time interval for illuminating the inside portion of the footwear 101 may be 5 seconds, 10 seconds and etc. In another embodiment, the light source 105 may illuminate the inside portion of the footwear 101 only when the user is wearing the footwear 101, thereby reducing the power consumption.

The communication unit 107 may be configured in the footwear 101 to enable the footwear 101 or the control unit 109 in the footwear 101 to communicate/connect to the computing device 201 associated with the user and/or the one or more care providers of the user. In an embodiment, the communication unit 107 may include, without limitation, the one or more wireless/air communication interfaces 209 such as, Wireless Local Area Network (LAN), Bluetooth and Wi-Fi. The communication unit 107 may be used to transfer the one or more captured images 125 and one or more notifications to the computing device 201.

In an embodiment, the control unit 109 is configured to receive the one or more images from the one or more image capturing devices 103. The one or more captured images 125 are compared with one or more pre-stored images 123 to identify one or more differences between the one or more captured images 125 and the one or more pre-stored images 123. The control unit 109 detects the health condition of the foot based on the one or more differences identified in the comparison. Further, the control unit 109 provides a notification about the health condition to the computing device 201 associated with the user or the one or more care providers of the user using the communication unit 107.

In an embodiment, the control unit 109 may include, but not limited to, a receiving module 113, a transmitting module 115, a pressure sensing module 117, a sensory module 119 and one or more other modules 121. In an embodiment, the other modules 121 may be used to perform various miscellaneous functionalities of the control unit 109 in the footwear 101. It will be appreciated that such aforementioned modules may be represented as a single module or a combination of different modules.

In an embodiment, the receiving module 113 may be configured to receive one or more inputs, signals and configuration settings from the computing device 201 through the communication unit 107. The configuration settings may include, without limitation, information about the computing device 201, and information about the user and/or one or more care providers of the user.

In an embodiment, the transmitting module 115 may be configured to transmit one or more data and signals to the one or more modules in the footwear 101. The transmitting module 115 may also transmit one or more images captured by the one or more image capturing device 103 to the computing device 201 using the communication unit 107.

In an embodiment, the pressure sensing module 117 may be placed at one or more predefined locations inside the footwear 101 to sense the presence of the foot of the user in the footwear 101. The pressure sensing module 117 is communicatively coupled to the control unit 109 and is responsible for actuating the one or more modules in the footwear 101. As an example, the pressure sensing module 117 may transmit a control signal to the control unit 109 to actuate each of the one or more image capturing devices 103 and the light source 105 upon detecting the presence of the foot in the footwear 101. In an embodiment, the pressure sensing module 117 may also measure the amount of pressure applied by body of the user on the foot and/or the pressure applied by the foot on the footwear 101 and captures the foot movement pattern.

Figure 3B:
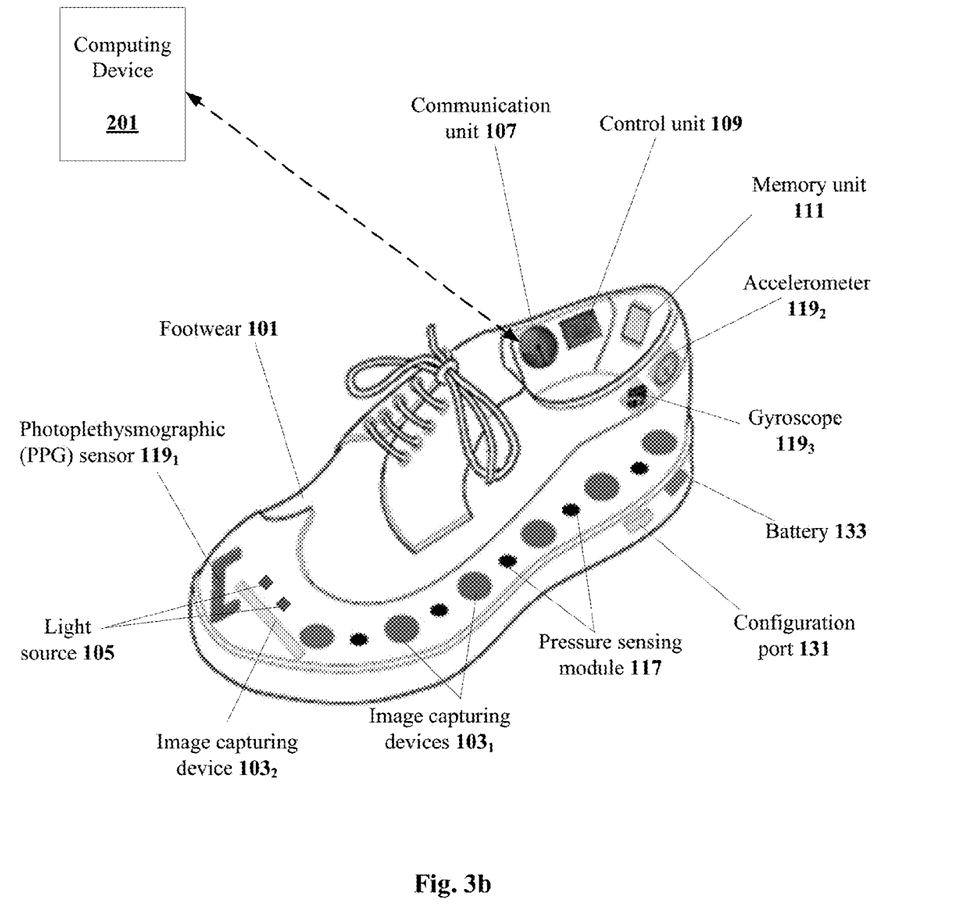

In an embodiment, the sensory module 119 comprises a Photo plethysmography (PPG) sensor $119_1$, an accelerometer $119_2$ and a gyroscope $119_3$ as shown in FIG. 3b. In an embodiment, the PPG sensors $119_1$ are placed inside the footwear 101, such that the PPG sensor $119_1$ touches/clamps to the toe of the user. The PPG sensor $119_1$ is used for optical detection of blood volume changes in the micro-vascular bed of tissue of the user. The PPG sensor $119_1$ may further comprise a light source and a detector, with infrared (IR) LEDs. The PPG sensor $119_1$ monitors changes in the light intensity via reflection from or transmission through the tissues of the user. The changes in light intensity are associated with small variations in blood perfusion of the tissue and provide information on the cardiovascular system, in particular, the pulse rate of the user. The PPG sensors $119_1$ are used in the footwear 101 due to their simplified working and their usefulness in monitoring the overall health condition of the user.

The accelerometer $119_2$ may be configured on a predefined location in the footwear 101 for measuring the acceleration of the foot of the user. In an embodiment, the accelerometer $119_2$ may also be used to measure/calculate the speed of walking and/or running of the user and to detect abnormalities, if any. In another embodiment, the accelerometer $119_2$ can be used to activate the system based on the movement detection.

The gyroscope $119_3$ may be configured on a predefined location in the footwear 101 for measuring the angular velocity of the foot of the user. In an embodiment, the gyroscope $119_3$ may also be used to detect and monitor vibrations of the foot inside the footwear 101.

In an embodiment, the sensory module 119 is used to measure current pressure, foot movement pattern and analyze them with historic data available in the memory and determines the quality of walking pattern. The sensory module 119 may also collect and measure heart rate data of the user with the historic data in the memory and provides a comparison analysis for the user. The heart rate data may also be used to detect Heart Rate Variability (HRV) and thereby, stress or fatigue levels of the user.

The memory unit 111 stores one or more pre-stored images 123, one or more captured images 125 of the foot, one or more configuration parameters 127 and other data 129.

In one embodiment, the data may be stored in the memory unit 111 in the form of various data structures. Additionally, the aforementioned data can be organized using data models, such as relational or hierarchical data models. The other data 129 may store data, including temporary data and temporary files, generated by modules for performing the various functions of control unit 109 in the footwear 101.

In an embodiment, the captured images 125 are the one or more images captured from the one or more image capturing devices 103. The one or more image capturing devices 103 capture the one or more images of the foot of the user when the user is wearing the footwear 101. The light source 105 configured in the footwear 101 illuminates the foot of the user for capturing clear and bright images of the foot. In an embodiment, the one or more image capturing devices 103 may capture the one or more images of the foot at predetermined time intervals. As an example, the predetermined time interval for capturing the new image of the foot may be 30 minutes.

Figure 2:
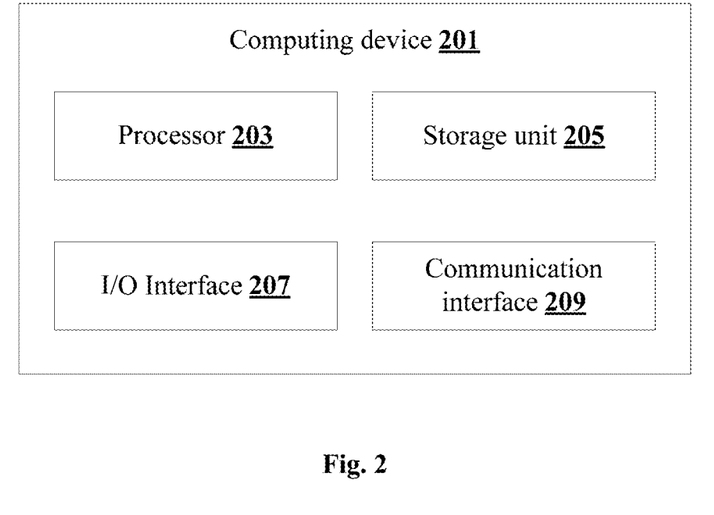
FIG. 2 shows a block diagram of a computing device associated with the user and/or one or more care providers of the user in accordance with some embodiments of the present disclosure.

In an embodiment, the pre-stored images 123 are the one or more images of the foot of the user which are captured when the foot of the user is in a healthy condition or shall act as a reference image, if the foot of the user is already damaged. The one or more captured images 125 are compared with the pre-stored images 123 to detect one or more disorders and/or variations in the foot. In another embodiment, the one or more pre-stored images 123 may be stored in the storage unit 205 of the computing device 201. In such a scenario, the control unit 109 transmits the one or more captured images 125 to the computing device 201 through the communication unit 107. Further, the processor 203 of the computing device 201 performs the comparison of the one or more captured images 125 with the pre-stored images 123 to detect one or more disorders in the foot. In an alternate embodiment, the computing device 201 can be part of the footwear 101.

In an embodiment, the one or more configuration parameters 127 are used to configure the footwear 101 as per the requirements of the user of the footwear 101. The user may configure the footwear 101 using a configuration port 131 in the footwear 101. The one or more configuration parameters 127 may include, but not limited to, one or more pre-stored images 123 of the foot, information of one or more care providers of the user, information of the computing device 201 and the predetermined intervals for capturing the images.

In an embodiment, the configuration port 131 is used to configure the footwear 101 with one or more configuration parameters 127 listed hereinabove. The configuration port 131 may also be used for configuring the communication unit 107 in the footwear 101. In an embodiment, the configuration port 131 may be a generic Universal Serial Bus (USB) port, which is also capable of charging a battery 133 in the footwear 101.

In an embodiment, the battery 133 may be used to power one or more image capturing devices 103, the light source 105 and the one or more modules in the control unit 109. The battery 133 may be rechargeable and/or replaceable when it is discharged completely.

FIG. 2 shows a block diagram of a computing device associated with the user and/or one or more care providers of the user in accordance with some embodiments of the present disclosure.

The computing device 201 associated with the user and/or the one or more care providers of the user may include, without limitation, a smart phone, a tablet phone, a Personal Digital Assistant (PDA) device, a laptop and a personal computer (PC). In an implementation, the computing device 201 comprises a processor 203, a storage unit 205, I/O interface 207 and a communication interface 209. The computing device 201 is communicatively associated to the footwear 101 and shall be capable of receiving one or more captured images 125 of the foot through the communication unit 107. The computing device 201 may also receive one or more notifications about the health condition of the foot of the user from the footwear 101.

In an embodiment, the processor 203 of the computing device 201 is capable of performing each of the functions performed by the control unit 109 in the footwear 101. The processor 203 may be connected with one or more input/output (I/O) devices via the I/O interface 207 for displaying the one or more captured images 125 to the user and/or the one or more care providers of the user.

In an embodiment, the storage unit 205 may store one or more pre-stored images 123 of the foot of the user. In another embodiment, the storage unit 205 of the computing device 201 may include, without limitation, memory drives, removable disc drives, etc., employing connection protocols such as Serial Advanced Technology Attachment (SATA), Integrated Drive Electronics (IDE), IEEE-1394, Universal Serial Bus (USB), fibre channel, Small Computer Systems Interface (SCSI) and the similar. The storage unit 205 may also store a collection of program or database components, including, without limitation, a User Interface (UI) application and an operating system.

In an embodiment, the I/O interface 207 may be used to display the one or more captured images 125, the pre-stored images 123 and the received notifications to the user and/or the one or more care providers of the user. The I/O interface 207 may employ communication protocols/methods such as, without limitation, audio, analog, digital, stereo, IEEE-1394, serial bus, Universal Serial Bus (USB), infrared, PS/2, BNC, coaxial, component, composite, Digital Visual Interface (DVI) and high-definition multimedia interface (HDMI).

In an embodiment, the communication interface 209 configured in the computing device 201 is capable of connecting to the communication unit 107 of the footwear 101 to receive and/or transmit the one or more captured images 125, the pre-stored images 123 and the notifications to the footwear 101. In an embodiment, the communication interface 209 may also be used to configure the footwear 101 before it is used by the user.

FIG. 3b shows exemplary representation of the footwear in accordance with some embodiments of the present disclosure.

The pressure sensing module 117 configured in the footwear 101 measures the amount of pressure applied on the footwear 101. The pressure sensing module 117 transmits a control signal to the control unit 109 upon detecting the presence of the user's foot in the footwear 101. The control unit 109, in response to the control signal from the pressure sensing module 117, actuates the one or more image capturing devices 103, the light source 105 and each of the modules in the footwear 101. The one or more image capturing devices 103 (plurality of cameras $103_1$ and an image scanner $103_2$ are shown in FIGS. 3a and 3b) capture the one or more images of the foot of the user upon actuation from the control unit 109 at predetermined time intervals. The light source 105 (not shown in figure) configured in the footwear 101 illuminates the foot of the user in order to capture a clear and bright image of the foot. In an embodiment, a transparent and/or translucent layer in the footwear 101 separates the one or more image capturing devices 103 and the light source 105 from the foot of the user when the user is wearing the footwear 101.

In an embodiment, the control unit 109 compares the one or more captured images 125 with one or more pre-stored images 123 to identify one or more differences between the one or more captured images 125 and the one or more pre-stored images 123. The one or more pre-stored images 123 are the images of the healthy foot of the user. The control unit 109 further detects the health condition of the foot of the user based on the one or more differences identified during the comparison. The detected health condition of the foot is notified to the computing device 201 associated with the user and/or the one or more care providers of the user through the communication unit 107. The user and/or the one or more care providers of the user may take necessary medical treatments if there are any disorders/diseases in the foot.

In another embodiment, upon capturing the one or more images of the foot, the one or more captured images 125 may be transmitted to the computing device 201 through the communication unit 107 configured in the footwear 101. The computing device 201 compares each of the one or more captured images 125 with the pre-stored images 123 of the healthy foot of the user to identify one or more diseases in the one or more captured images 125.

In an embodiment, the sensory module 119 configured in the footwear 101 measure one or more other health parameters related to the user. The PPG sensor $119_1$ configured in the footwear 101 measures the heart rate and level of oxygen in the blood of the user. The accelerometer $119_2$ measures the acceleration of the foot of the user. The gyroscope $119_3$ measures the angular velocity of the foot of the user. The one or more health parameter data, measured by each of the sensory module 119 may be transmitted to the computing device 201 to notify the user and/or the one or more care providers of the user about the measured health parameter data.

In an embodiment, the user and/or the one or more care providers of the user may provide one or more feedback to the notification received from the footwear 101. The control unit 109 configured in the footwear 101 improves accuracy of monitoring the foot health based on the one or more feedback received from the user on the notification. The quality of the notification is identified by using the explicit feedback from the user and the same is captured onto a self-learning component in the control unit 109 of the footwear 101. For each notification with poor feedbacks, the self-learning component identifies a key root cause for the wrong analysis and compares the notifications made at different stages of monitoring. Accordingly, the self-learning component improves the quality of the notifications provided to the users.

Figure 4:
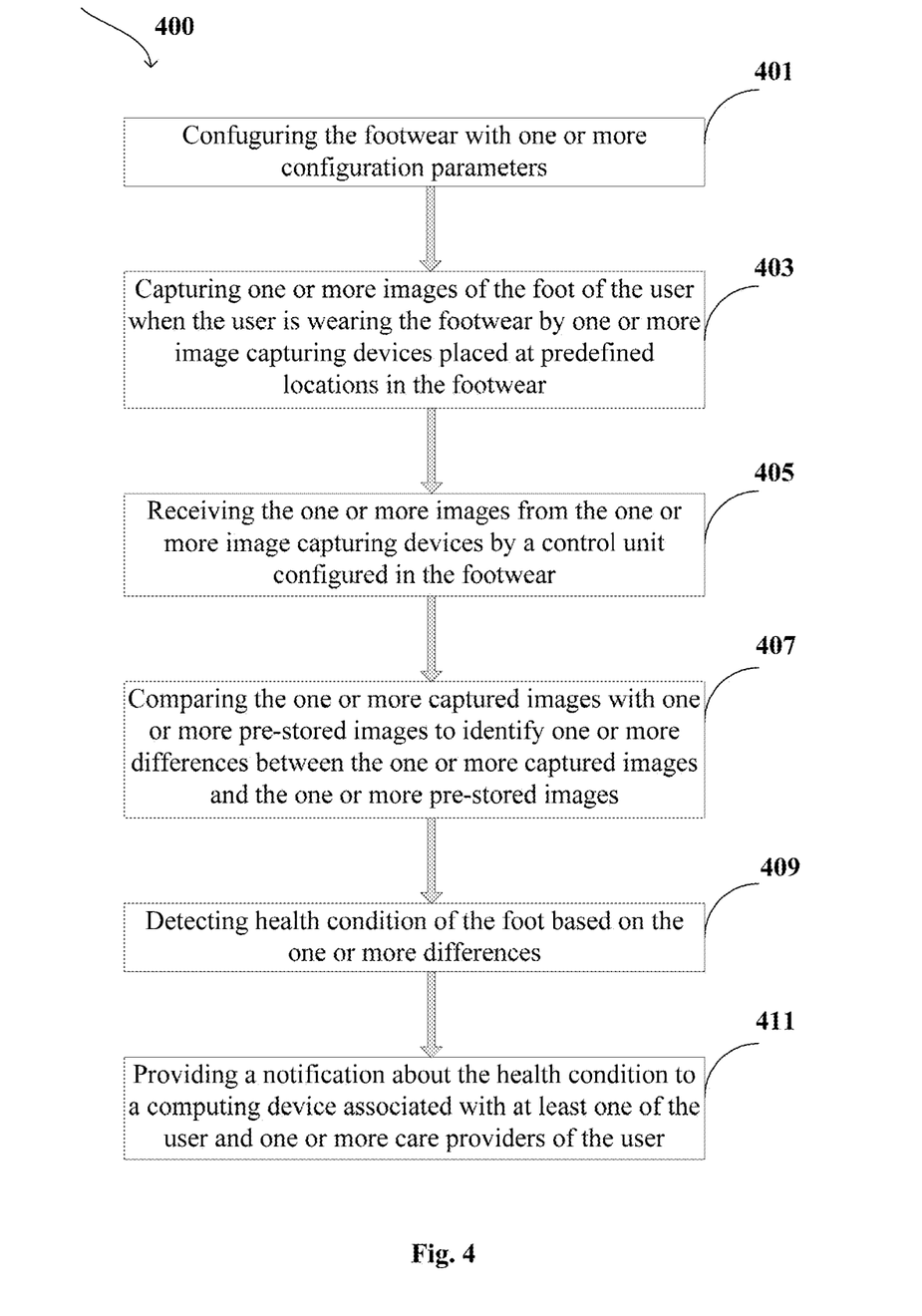
FIG. 4 illustrates a flowchart showing a method for monitoring health condition of foot of a user in accordance with some embodiments of the present disclosure.

FIG. 4 illustrates a flowchart showing a method for monitoring health condition of foot of a user in accordance with some embodiments of the present disclosure.

As illustrated in FIG. 4, the method 400 comprises one or more blocks for monitoring the health condition of foot of the user, when the user is wearing the footwear 101. The method 400 may be described in the general context of computer executable instructions. Generally, computer executable instructions can include routines, programs, objects, components, data structures, procedures, modules, and functions, which perform particular functions or implement particular abstract data types.

The order in which the method 400 is described is not intended to be construed as a limitation, and any number of the described method blocks can be combined in any order to implement the method. Additionally, individual blocks may be deleted from the methods without departing from the spirit and scope of the subject matter described herein. Furthermore, the method can be implemented in any suitable hardware, software, firmware, or combination thereof.

At block 401, the footwear 101 is configured with one or more configuration parameters 127. The one or more configuration parameters 127 comprises at least one of the one or more pre-stored images 123 of the foot of the user, the predefined time intervals for capturing the image of the foot, information of one or more care providers and information of the computing device 201. The configuration of the footwear 101 may be achieved through a configuration port 131 in the footwear 101.

At block 403, one or more image capturing devices 103 placed at predefined locations in the footwear 101 capture the one or more images of the foot of the user when the user is wearing the footwear 101. The one or more image capturing devices 103 are actuated by the control unit 109 when the control unit 109 receives a control signal from the pressure sensing module 117. The pressure sensing module 117 sends the control signal to the control unit 109 upon detecting the presence of user's foot in the footwear 101. The light source 105 in the footwear 101 illuminates the foot of the user for enabling the one or more image capturing devices 103 to capture clear picture of the foot.

At block 405, the control unit 109 configured in the footwear 101 receives the one or more captured images 125 from the one or more image capturing devices 103. The one or more image capturing devices 103 is configured to capture the image of the foot at one or more predefined time intervals. Further, the footwear 101 also comprises a transparent layer, wherein the transparent layer separates the foot of the user and each of the one or more image capturing devices 103.

At block 407, the control unit 109 configured in the footwear 101 compares the one or more captured images 125 with one or more pre-stored images 123 to identify one or more differences between the one or more captured images 125 and the one or more pre-stored images 123, wherein the one or more pre-stored images 123 are the images of healthy foot of the user.

At block 409, the control unit 109 configured in the footwear 101 detects health condition of the foot of the user based on the one or more differences. The health condition of the foot of the user may also be determined with the help of one or more health parameter data obtained by the sensory module 119.

At block 411, the control unit 109 provides a notification about the health condition of the foot to a computing device 201 associated with at least one of the user and one or more care providers of the user. The footwear 101 and the computing device 201 are connected through the communication unit 107. The communication unit 107 may also transmit the one or more captured images 125 to the computing device 201.

Advantages of the Embodiment of the Present Disclosure are Illustrated Herein

In an embodiment, the present disclosure provides a method and footwear for monitoring health condition of the foot of a user.

In an embodiment, the present disclosure provides a method for providing a real time notification about the health condition of the foot of the user to the user and/or one or more care providers of the user.

In an embodiment, the footwear disclosed in the present disclosure comprises one or more sensory modules for detecting/measuring one or more critical health parameters of the user.

In an embodiment, the present disclosure provides a convenient method of monitoring the foot health of the user requiring no/minimum efforts and/or intervention of the user.

The terms "an embodiment", "embodiment", "embodiments", "the embodiment", "the embodiments", "one or more embodiments", "some embodiments", and "one embodiment" mean "one or more (but not all) embodiments of the invention(s)" unless expressly specified otherwise.

The terms "including", "comprising", "having" and variations thereof mean "including but not limited to", unless expressly specified otherwise.

The enumerated listing of items does not imply that any or all of the items are mutually exclusive, unless expressly specified otherwise.

The terms "a", "an" and "the" mean "one or more", unless expressly specified otherwise.

A description of an embodiment with several components in communication with each other does not imply that all such components are required. On the contrary a variety of optional components are described to illustrate the wide variety of possible embodiments of the invention.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article or a different number of devices/articles may be used instead of the shown number of devices or programs. The functionality and/or the features of a device may be alternatively embodied by one or more other devices which are not explicitly described as having such functionality/features. Thus, other embodiments of the invention need not include the device itself.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present invention are intended to be illustrative, but not limiting, of the scope of the invention, which is set forth in the following claims.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

| Referral Numerals: | |
|---|---|
| Reference Number | Description |
| 101 | Footwear |
| 103 | Image capturing devices |
| 105 | Light source |
| 107 | Communication unit |
| 109 | Control unit |
| 111 | Memory unit |
| 113 | Receiving module |
| 115 | Transmitting module |
| 117 | Pressure sensing module |
| 119 | Sensory module |
| 121 | Other modules |
| 123 | Pre-stored images |
| 125 | Captured images |
| 127 | Configuration parameters |
| 129 | Other data |
| 131 | Configuration port |
| 133 | Battery |
| 201 | Computing device |
| 203 | Processor |
| 205 | Storage unit |
| 207 | I/O Interface |
| 209 | Communication interface |

What is claimed is:

1. Footwear for monitoring a health condition of a foot of a user, the footwear comprising:
   one or more image capturing devices placed at predefined locations in the footwear to capture one or more images of the foot of the user, when the user is wearing the footwear; and
   a control unit configured to:
      receive the one or more images from the one or more image capturing devices;
      compare the one or more captured images with one or more pre-stored images to identify one or more differences between the one or more captured images and the one or more pre-stored images, wherein the one or more pre-stored images are the images of healthy foot of the user;
      detect a health condition of the foot of the user based on the one or more differences; and
      provide a notification about the health condition of the foot to a computing device associated with at least one of the user and one or more care providers of the user.

2. The footwear as claimed in claim 1, wherein each of the one or more image capturing devices comprises a light source for illuminating the foot.

3. The footwear as claimed in claim 1 further comprises a transparent layer, wherein the transparent layer separates the foot of the user and each of the one or more image capturing devices.

4. The footwear as claimed in claim 1, wherein each of the one or more image capturing devices captures the image of the foot at one or more predefined time intervals.

5. The footwear as claimed in claim 1 further comprises a pressure sensor to:
   detect the presence of the foot of the user in the footwear; and
   transmit a control signal to the control unit upon detecting the presence of the foot of the user in the footwear.

6. The footwear as claimed in claim 5, wherein the control unit actuates each of the one or more image capturing devices and the light source upon receiving the control signal from the pressure sensor.

7. The footwear as claimed in claim 1 further comprises a communication unit, to transmit the one or more captured images and the notification to the computing device.

8. The footwear as claimed in claim 1 further comprises a battery to power the footwear and a charging port to recharge the battery.

9. The footwear as claimed in claim 1 further comprises a configuration port to configure the footwear with one or more configuration parameters.

10. The footwear as claimed in claim 9, wherein the one or more configuration parameters comprises at least one of the one or more pre-stored images of the foot of user, the predefined time intervals for capturing the image of the foot, information of one or more care providers and information of the computing device.

11. The footwear as claimed in claim 1, wherein the control unit is further configured to receive feedback from the user based on the notification, for improving accuracy of monitoring.

12. The footwear as claimed in claim 1 further comprises a memory unit for storing the one or more pre-stored images and the one or more captured images, wherein the memory unit is communicatively interfaced with the control unit.

13. A method for monitoring a health condition of foot of a user, the method comprising:
   capturing, by one or more image capturing devices placed at predefined locations in footwear, one or more images of the foot of the user when the user is wearing the footwear;
   receiving, by a control unit configured in the footwear, the one or more images from the one or more image capturing devices;
   comparing, by the control unit, the one or more captured images with one or more pre-stored images to identify one or more differences between the one or more captured images and the one or more pre-stored images, wherein the one or more pre-stored images are the images of a healthy foot of the user;
   detecting, by the control unit, a health condition of the foot based on the one or more differences; and providing, by the control unit, a notification about the health condition to a computing device associated with at least one of the user and one or more care providers of the user.

14. The method as claimed in claim 13 further comprises illuminating the foot using a light source configured in each of the one or more image capturing devices.

15. The method as claimed in claim 13, wherein the one or more the images of foot are captured by the one or more image capturing devices at one or more predefined time intervals.

16. The method as claimed in claim 13 further comprises:
detecting, by a pressure sensor configured in the footwear, a presence of the foot of the user in the footwear; and
transmitting, by the pressure sensor, a control signal to the control unit upon detecting the presence of the foot of the user in the footwear.

17. The method as claimed in claim 16 further comprises actuating, by the control unit, each of the one or more image capturing devices and a light source upon receiving the control signal from the pressure sensor.

18. The method as claimed in claim 13 further comprises configuring the footwear with one or more configuration parameters using a configuration port in the footwear.

19. The method as claimed in claim 18, wherein the one or more configuration parameters comprises at least one of the one or more pre-stored images of the foot of the user, the predefined time intervals for capturing the image of the foot, information of one or more care providers and information of the computing device.

20. The method as claimed in claim 13 further comprises transmitting the one or more captured images and the notification to the computing device using a communication unit configured in the footwear.

21. The method as claimed in claim 13 further comprises storing the one or more pre-stored images and the one or more captured images in a memory unit, wherein the memory unit is communicatively interfaced with the control unit.

22. The method as claimed in claim 13 further comprises receiving feedback from the user based on the notification, for improving accuracy of monitoring.

* * * * *